United States Patent
Sherman

(10) Patent No.: US 10,898,512 B2
(45) Date of Patent: *Jan. 26, 2021

(54) INTRADIALYTIC USE OF SODIUM NITRITE

(71) Applicant: Hope Medical Enterprises, Inc., Scottsdale, AZ (US)

(72) Inventor: Craig Sherman, Scottsdale, AZ (US)

(73) Assignee: Hope Medical Enterprises, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,428

(22) Filed: May 3, 2019

(65) Prior Publication Data

US 2019/0255098 A1 Aug. 22, 2019

Related U.S. Application Data

(63) Continuation of application No. 15/914,353, filed on Mar. 7, 2018, now Pat. No. 10,328,099.

(60) Provisional application No. 62/468,857, filed on Mar. 8, 2017.

(51) Int. Cl.
*A61K 33/00* (2006.01)
*A61M 1/16* (2006.01)

(52) U.S. Cl.
CPC ............ *A61K 33/00* (2013.01); *A61M 1/1654* (2013.01)

(58) Field of Classification Search
CPC ......... A61K 33/00; A61K 1/1654; A61P 9/10; A61P 9/00
See application file for complete search history.

(56) References Cited

U.S. PATENT DOCUMENTS

| | | | |
|---|---|---|---|
| 5,843,316 A | 12/1998 | Kurittu | |
| 8,216,776 B2 | 7/2012 | Sakai et al. | |
| 8,496,973 B2 | 7/2013 | Sherman | |
| 8,568,793 B2 | 10/2013 | Sherman | |
| 8,715,746 B2 | 5/2014 | Sherman et al. | |
| 8,920,852 B2 | 12/2014 | Sherman et al. | |
| 9,144,580 B2 | 9/2015 | Sherman et al. | |
| 9,283,249 B2 | 3/2016 | Sherman et al. | |
| 9,345,724 B2 | 5/2016 | Sherman et al. | |
| 9,504,709 B2 | 11/2016 | Sherman et al. | |
| 9,579,345 B2 | 2/2017 | Sherman et al. | |
| 9,579,354 B2 | 2/2017 | Clements et al. | |
| 9,585,912 B2 | 3/2017 | Sherman et al. | |
| 9,687,505 B2 | 6/2017 | Sherman et al. | |
| 9,687,506 B2 | 6/2017 | Sherman et al. | |
| 9,944,524 B2 | 4/2018 | Sherman et al. | |
| 10,328,099 B2 * | 6/2019 | Sherman .............. | A61M 1/1654 |
| 2007/0154570 A1 | 7/2007 | Miller et al. | |
| 2007/0199898 A1 | 8/2007 | Sakai et al. | |
| 2009/0304600 A1 | 12/2009 | Shetty | |
| 2010/0247682 A1 | 9/2010 | Gladwin et al. | |

(Continued)

OTHER PUBLICATIONS

Include (The American Heritage Dictionary 2nd College Edition 1982, Houghton Mifflin Company). 3 pages (Year: 1982).*
Bryan et al., "Acute effects of hemodialysis on nitrite and nitrate: potential cardiovascular implications in dialysis patients", Free Radical Biology Medicine, 58:46-51 (2013).

(Continued)

*Primary Examiner* — Ernst V Arnold
(74) *Attorney, Agent, or Firm* — Jones Day

(57) ABSTRACT

Provided herein are methods for maintaining physiological levels of nitrite in a subject undergoing hemodialysis. Also provided herein are methods of administering pharmaceutically acceptable sodium nitrite to a subject undergoing hemodialysis.

19 Claims, 1 Drawing Sheet

(56) References Cited

U.S. PATENT DOCUMENTS

2012/0321724 A1  12/2012  Bryan
2014/0350097 A1  11/2014  Lai
2017/0252368 A1   9/2017  Sherman et al.

OTHER PUBLICATIONS

Inrig et al., "Effect of low versus high dialysate sodium concentration on blood pressure and endothelial-derived vasoregulators during hemodialysis: a randomized crossover study", American Journal of Kidney Diseases, 65(3):464-473 (2015).
Locatelli et al., "Optimizing haemodialysate composition", Clinical Kidney Journal, 8(5):580-589.
Sam et al., "Composition and clinical use of hemodialysates", Hemodialysis International, 10(1):15-28 (2006).
International Search Report and Written Opinion of corresponding PCT Application No. PCT/US2018/021053 dated May 3, 2018 (6 pages).
International Search Report and Written Opinion of corresponding PCT Application No. PCT/US2018/021069 dated May 30, 2018 (14 pages).
Zhou et al., Water-Soluble Poly(ethylenimine)-Based Nitric Oxide Donors: Preparation, Characterization, and Potential Application in Hemodialysis, Biomacromolecules, 7:2565-2574 (2006).
Carlström et al., "Peritoneal dialysis impairs nitric oxide homeostasis and may predispose infants with low systolic blood pressure to cerebral ischemia", Nitric Oxide, 58:1-9 (2016).
Supplemental European Search Report and European Search Opinion of corresponding European Application No. 18763384.7 dated Nov. 24, 2020 (10 pages).

\* cited by examiner

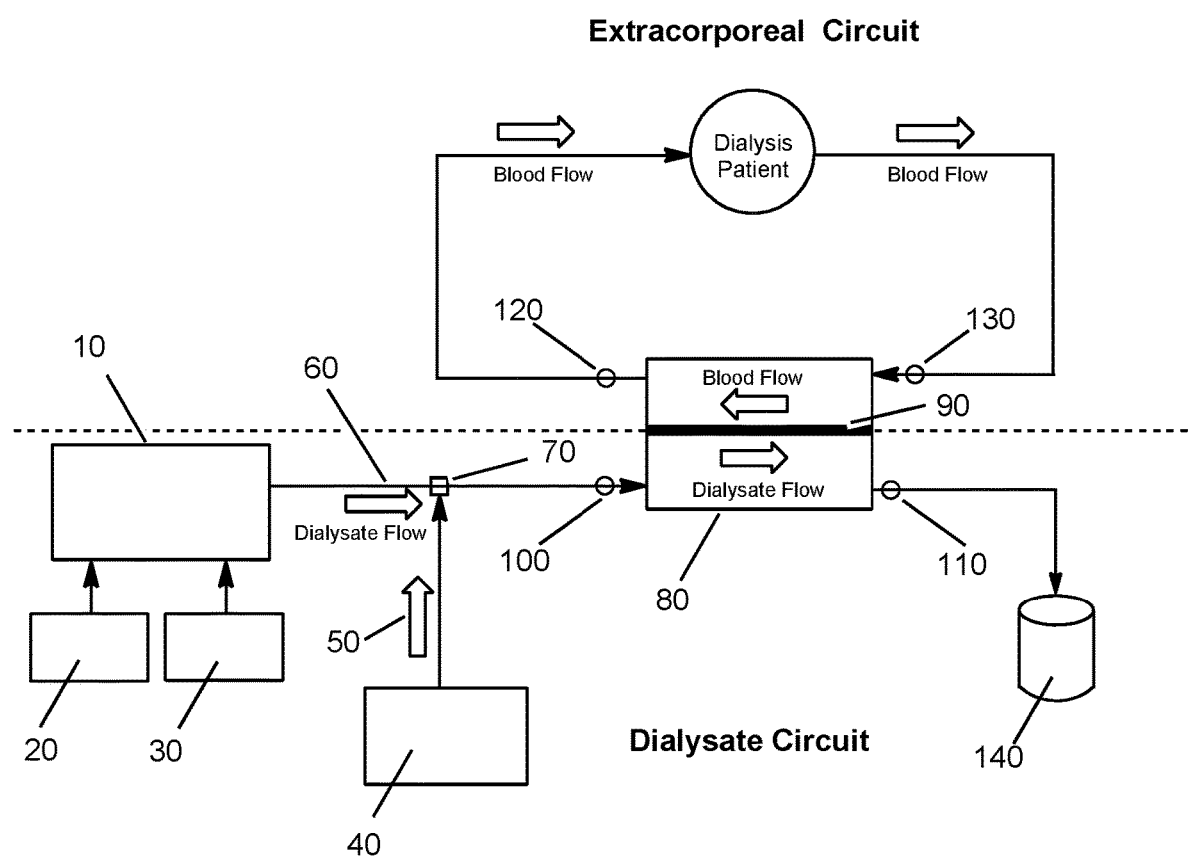

INTRADIALYTIC USE OF SODIUM NITRITE

CROSS REFERENCE

This application is a continuation of U.S. patent application Ser. No. 15/914,353, filed Mar. 7, 2018, now U.S. Pat. No. 10,328,099, which claims the benefit of priority of U.S. Provisional Patent Application No. 62/468,857, filed Mar. 8, 2017, the content of each of which are incorporated herein by reference in its entirety.

FIELD

Provided herein are methods for maintaining physiological levels of nitrite in a subject undergoing hemodialysis. Also provided herein are methods of administering pharmaceutically acceptable sodium nitrite to a subject undergoing hemodialysis.

BACKGROUND

Patients with chronic kidney disease (CKD) experience deterioration of kidney function which results in a reduction in the excretion of metabolic waste products. The accumulation of metabolic waste products can become life threatening within days. Patients with little or no residual kidney function are characterized as having "end-stage renal disease." Therefore, such patients need an alternative means to excrete waste products to survive. Dialysis is a means to excrete waste products that involves the transfer of waste products from the blood to an external liquid that is subsequently discarded (*Am. J. Kidney Dis.* 2002, 39(Suppl. 1), S1-266).

Dialysis is defined as the movement of solutes and water between two liquids that are separated by a semipermeable "dialyzer membrane." In hemodialysis, blood flows across one side of the dialyzer membrane while a water-based solution called dialysate flows across the other side. Dialyzer membranes contain pores through which solutes can pass. The concentrations of solutes that are present in these two liquids equilibrate as osmotic forces push them out of the high concentration liquid, through the dialyzer membrane pores, and into the low concentration liquid.

Dialyzer membranes are designed with different pore sizes to limit the solutes that can pass through during hemodialysis. During hemodialysis, it may be harmful to remove from the blood an excessive amount of small molecule solutes, which can diffuse through dialyzer membrane.

Blood contains small molecular weight solutes such as nitrite ($NO_2^-$). Nitrite anions have a molecular weight of 46 Daltons. Nitrite has been determined to be a physiological reservoir for nitric oxide in humans (Gladwin, PCT/US2004/021985, Filing date Jul. 9, 2004). The concentration of nitrite in the blood of healthy individuals is approximately 300 nanomolar.

The Association for the Advancement of Medical Instrumentation (AAMI) established a quality specification limit for the nitrate content in water that is used in dialysis (maximum 2 mg per liter, i.e. 2 ppm) (# ANSI/AAMI/ISO 13959:2009). The AAMI also specified that the nitrate content in water should be measured using the "cadmium reduction method". In this method, a sample is passed through a column containing granulated copper-cadmium to reduce nitrate to nitrite. The nitrite is subsequently determined by diazotizing with sulfanilamide and coupling with N-(1-naphthyl)-ethylenediamine dihydrochloride to form a highly colored azo dye, which is measured with a spectrometer (U.S. Environmental Protection Agency. National Environmental Methods Index. Available online at www.nemi.gov/methods/method_summary/5121). This test method does not distinguish between nitrate and nitrite. Instead, it is actually a measurement of both nitrate and nitrite. Therefore, the AAMI quality specification for nitrate limits the sum of nitrate and nitrite in water that is used in dialysis as the test method specified by AAMI does not distinguish between nitrate and nitrite. Therefore, the AAMI quality specification for nitrate is actually a limit of the sum of nitrate and nitrite in water that is used in dialysis.

Myocardial infarction has been associated with reduced blood nitrite levels (Kehmeier et al., *Free Radic. Biol. Med.* 2008, 44, 1945-1950). In myocardial ischemia, nitrite is reduced to nitric oxide. Since nitric oxide is a vasodilator, the reduction of nitrite to nitric oxide protects cardiac function by increasing blood flow to ischemic tissues. This beneficial effect exists as long as nitrite remains available in the blood. Nitrite depletion may be a contributing factor in the progression of tissue ischemia to infarction when vasodilation cannot be sustained (Landmesser et al., *Curr. Opin. Cardiol.* 2005, 20, 547-551).

Cardiovascular disease accounts for more than half of all deaths of patients who require chronic hemodialysis (Go et al., *N. Eng. J. Med.* 2004, 351, 1296-1305). There was a 1.7 fold increased risk of sudden death events in the 12 hour period beginning with the dialysis treatment. Sudden death events were increased both during the dialysis procedure itself and after treatment (Bleyer et al., *Kidney Int.* 2006, 12, 2268-2273).

Coincidentally, the concentration of nitrite in the plasma declines by over 60% during the first hour of hemodialysis and remains significantly depressed during the subsequent hours of a four-hour hemodialysis session (Bryan et al., *Free Radic. Biol. Med.* 2013, 58, 46-51)

Sodium nitrite can be administered into the blood by intravenous injection; however, it would be ineffective in maintaining physiological levels with dialysis patients since it is rapidly removed during hemodialysis. At this time, there is no effective method for maintaining physiological levels of nitrite in the blood of patients who undergo hemodialysis. There is also no satisfactory method for administrating sodium nitrite to patients during hemodialysis.

SUMMARY

The present disclosure provides methods for maintaining physiological levels of nitrite in a subject undergoing hemodialysis. The present disclosure also provides methods for preventing myocardial infarction, sudden cardiac death, stroke, cardiovascular disease, high blood pressure, pulmonary hypertension, and/or renal hypertension in a subject undergoing hemodialysis. The present disclosure also provides methods for administering sodium nitrite in a subject undergoing hemodialysis.

In some embodiments, provided herein are methods for maintaining physiological levels of nitrite in a subject undergoing hemodialysis, comprising intradialytically contacting said subject's blood with a dialyzer membrane that is also in contact with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for maintaining physiological levels of nitrite in a subject undergoing hemodialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for preventing myocardial infarction in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for preventing sudden cardiac death in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for preventing stroke in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for preventing cardiovascular disease that is characterized by tissue ischemia including angina, cerebral vasospasm, claudication, critical limb ischemia, peripheral vascular disease, and sickle cell crisis in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for preventing high blood pressure, pulmonary hypertension, and renal hypertension in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, also provided herein are methods for administering sodium nitrite to a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

BRIEF DESCRIPTION OF THE DRAWINGS

FIG. 1. is a schematic diagram of elements of the flow path of the dialysate, the blood of patients, and the aqueous solution comprising sodium nitrite. (10) Dialysis machine; (20) acid concentrate solution; (30) bicarbonate concentrate solution; (40) aqueous solution comprising sodium nitrite; (50) flow of aqueous solution comprising sodium nitrite; (60) dialysate tubing; (70) valve; (80) dialyzer; (90) dialyzer membrane; (100) detection point "pre" dialyzer membrane; (110) detection point "post" dialyzer membrane; (120) detection point "V"; (130) detection point "A"; (140) used dialysate.

DETAILED DESCRIPTION

The following detailed description is not to be taken in a limiting sense, but is made merely for the purpose of illustrating the embodiments provided herein.

To facilitate understanding of the disclosure set forth herein, a number of terms are defined below.

Generally, the nomenclature used herein and the laboratory procedures in inorganic chemistry, analytical chemistry, organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject. In one embodiment, the subject has or is at risk for a disease, disorder or condition provided herein. In another embodiment, the subject has or is at risk for a disease, disorder or condition wherein the disease, disorder or condition, or a symptom thereof, can be treated, prevented or ameliorated by the administration of sodium nitrite. In another embodiment, the subject is an end stage renal disease (ESRD) patient who is placed on regular hemodialysis. In another embodiment, the subject is a patient with some or no renal function who undergoes dialysis to reduce wastes from the blood to safe levels. In another embodiment, the steady-state plasma and saliva concentration of nitrite in the subject undergoing hemodialysis are significantly reduced as a result of about 3 to about 5 hours of hemodialysis. In another embodiment, the subject has plasma levels of nitrite that are below normal physiological levels.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

In general, conventional dialysates are defined as any formulation heretofore known, whether or not proprietary, including those that are recently patented. Many of these are specially formulated to satisfy the needs of a particular type. For example, U.S. Pat. No. 6,436,969 discloses compositions containing AGE inhibitors, U.S. Pat. No. 5,869,444 claims solutions contain an osmotically effective mixture of peptides, U.S. Pat. Nos. 6,306,836 and 6,380,163 disclose peritoneal dialysis solution utilizing amino acids to achieve osmotic balance.

The term "bicarbonate concentrate solution" refers to aqueous solution comprising a bicarbonate salt or a mixture of bicarbonate salts and water that meets or exceeds the current hemodialysis water quality standards as listed in ANSI/AAMI/ISO #13959:2009 (hereafter called "purified water"). Minntech Renal Systems in Minneapolis, Minn. supplies Centrisol® Bicarbonate Concentrate Powder MB-330. Each bag of Centrisol® Bicarbonate Concentrate Powder 45X MB-330 contains about 650 grams of sodium bicarbonate. The contents of a bag are mixed with purified water to make about 8 liters of dialysate bicarbonate concentrate solution.

The term "acid concentrate solution" refers to aqueous solution comprising acid or a mixture of acids and purified water. Representative examples of acid include, but are not limited to hydrochloric acid, acetic acid, citric acid, and peracetic acid. Minntech Renal Systems in Minneapolis, Minn. supplies Centrisol® Acid Concentrate 45X SB-111. Each bag of Centrisol® Acid Concentrate Powder 45X contains acetate, bicarbonate, calcium, chloride, dextrose, magnesium, and potassium. One volume part of acid concentrate should be mixed with 1.72 volume parts of properly mixed MB-330 Series Sodium Bicarbonate Concentrate and 42.28 volume parts of purified water to prepare 45 volume parts of dialysate solution.

The term "dialysis machine" is a machine comprising an extracorporeal circuit and a dialysate circuit. The extracorporeal circuit further comprises tubing, blood pump, heparin pump, kidney, and monitors for blood flow, blood pressure, and air bubbles. The dialysate circuit further comprises dialysate tubing, dialysate pump, and monitors for dialysate flow, dialysate pressure, and air bubbles. Presently, dialysis machines utilize an automated proportioning system to mix the acid concentrate solution, bicarbonate concentrate solution and purified water in specific proportions to general the dialysate. The dialysate concentrate solutions (acid and bicarbonate) are usually supplied by the manufacturer either as a premixed powder (as bicarbonate powder) that is added to purified water in large reservoirs or as a solution (as acid concentrate) ready to use. The dialysate concentrate solutions are pumped into a chamber in the dialysis machine where they are mixed with purified water to make the dialysate.

The term "dialysate tubing" refers to the tubing connects a dialysis machine and a dialyzer.

The term "dialyzer" is meant to include an artificial kidney comprising a synthetic or semi-synthetic semipermeable membrane (hereafter called "dialyzer membrane") made of chemical materials including but not limited to cellulose acetate, cupraphane, polyacrilonitrile, polymethyl methacrylate, or polysulfone. A constant flow of blood on one side the membrane and dialysate on the other allows removal of wastes in the blood. An artificial kidney can be used to perform hemodialysis, during which diffusion is the major mechanism for solute removal. On the other hand hemofiltration (also called hemodiafiltration and diafiltration) relies on ultrafiltration and convective transport rather than diffusion to move solutes across a high porosity semipermeable membrane.

The term "unspiked dialysate" refers to the dialysate solution mixed by the dialysis machine and pumped into the dialysate tubing to flow to the dialyzer membrane before the aqueous solution comprising sodium nitrite is added to the dialysate tubing through a valve.

The term "nitrite-spiked dialysate" refers to dialysate solution in the dialysate tubing after the aqueous solution comprising sodium nitrite is added to the dialysate tubing through a valve.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician. In one embodiment, a therapeutically effective amount is an amount sufficient to maintain a subject's blood level of nitrite at about physiological levels.

The term "about" or "approximately" means an acceptable error for a particular value as determined by one of ordinary skill in the art, which depends in part on how the value is measured or determined. In some embodiments, the term "about" or "approximately" means within 1, 2, 3, or 4 standard deviations. In some embodiments, the term "about" or "approximately" means within 15%, 10%, 9%, 8%, 7%, 6%, 5%, 4%, 3%, 2%, 1%, 0.5%, or 0.05% of a given value or range. In some embodiments, it is contemplated that the values preceded by the term "about" or "approximately" are exact.

The term "normal physiological levels" of nitrite means the levels of nitrite that occur in a healthy adult subject. In one embodiment, the normal physiological level of nitrite in a subject is about 300 nanomolar.

Sodium Nitrite

In some embodiments, the methods provided herein comprise the use of purified forms of sodium nitrite ($NaNO_2$), also known as monosodium salt of nitrous acid. In one embodiment, provided herein is pharmaceutically acceptable sodium nitrite. In another embodiment, provided herein are forms of sodium nitrite meeting one, more than one, or all FDA standards for sodium nitrite for pharmaceutical use. In one embodiment, the pharmaceutically acceptable sodium nitrite is that disclosed in U.S. Pat. Pub. No. 2010/0203172, filed Feb. 10, 2010, which is incorporated by reference herein in its entirety.

In one embodiment, the pharmaceutically acceptable sodium nitrite is white to off-white solid.

In one embodiment, the pharmaceutically acceptable sodium nitrite has a positive identification test for sodium determined according to method <191> in USP XXXII (2009).

In one embodiment, the pharmaceutically acceptable sodium nitrite has a positive identification test for nitrite determined according to method <191> in USP XXXII (2009).

In one embodiment, the sodium nitrite provided herein contains no less than about 97% by weight and/or no greater than about 101% by weight of sodium nitrite. In some embodiments, the amount of sodium nitrite in the sodium nitrite provided herein is determined according to USP colorimetric assay (USP XXXII (2009)). In some embodiments, the amount of sodium nitrite in the sodium nitrite provided herein is determined by an ion chromatography. In some embodiments, the amount of sodium nitrite in the sodium nitrite provided herein is determined by an ion chromatography is coupled with suppressed conductivity detection as described herein.

In another embodiment, the sodium nitrite provided herein has a pH between about 7 to about 9 when measured in a 10% solution at 25° C. In some embodiments, the pH of the sodium nitrite provided herein is measured using a pH meter. In some embodiments, the pH of the sodium nitrite provided herein is determined according to Method 791 in USP XXXII (2009).

In yet another embodiment, the sodium nitrite provided herein has a loss on drying of no greater than about 0.25% by weight. In some embodiments, the loss on drying of the sodium nitrite provided herein is quantitated according to Method 731 in USP XXXII (2009).

In yet another embodiment, the sodium nitrite provided herein has water content of no greater than about 0.5% by weight. In some embodiments, the water content in the sodium nitrite provided herein is determined by Karl Fischer method. In some embodiments, the water content in the sodium nitrite provided herein is quantitated according to Method 921 in USP XXXII (2009).

In yet another embodiment, the heavy metal content in the sodium nitrite provided herein is no greater than about 10 ppm of a heavy metal. The heavy metal content in the sodium nitrite provided herein is determined according to Method 231 in USP XXXII (2009).

In yet another embodiment, the sodium nitrite provided herein contains no greater than about 0.4% by weight of sodium nitrate. In some embodiments, the amount of sodium nitrate in the sodium nitrite provided herein is determined by an ion chromatography method in coupled with suppressed conductivity detection as described herein.

In yet another embodiment, the sodium nitrite provided herein contains no greater than about 0.02% by weight of sodium carbonate. In some embodiments, the amount of sodium carbonate in the sodium nitrite provided herein is determined by mixing the sample with an acid to convert carbonate to carbon dioxide and venting the carbon dioxide to a non-dispersive infrared detector for measurement.

In yet another embodiment, the sodium nitrite provided herein contains no greater than about 0.005% by weight of insoluble matter. In some embodiments, the amount of insoluble material in the sodium nitrite provided herein is determined by dissolving 10 grams of the sodium nitrite provided herein in 100 mL of water, the solution is heated to boiling for 1 hour, the solution is filtered, washed with hot water, dried, cooled in a desiccator, and weighed.

In yet another embodiment, the sodium nitrite provided herein contains no greater than about 0.005% by weight of chloride. In some embodiments, the chloride content in the sodium nitrite provided herein is determined according to Method 221 in USP XXXII (2009).

In yet another embodiment, the sodium nitrite provided herein contains no greater than about 0.01% by weight of sulfate. In some embodiments, the sulfate content in the sodium nitrite provided herein is determined according to Method 221 in USP XXXII (2009).

In yet another embodiment, the sodium nitrite provided herein contains no greater than about 0.001% by weight of iron. In some embodiments, the iron content in the sodium nitrite provided herein is determined using inductively coupled plasma mass spectrometry (ICP-MS). In some embodiments, the iron content in the sodium nitrite provided herein is determined using inductively coupled plasma-optical emission spectroscopy (ICP-OES). In some embodiments, the iron content in the sodium nitrite provided herein is determined according to Method 241 in USP XXXII (2009).

In yet another embodiment, the sodium nitrite provided herein contains no greater than about 0.01% by weight of calcium. In some embodiments, the calcium content in the sodium nitrite provided herein is determined using ICP-MS. In some embodiments, the calcium content in the sodium nitrite provided herein is determined using flame emission spectrometry (FES).

In yet another embodiment, the sodium nitrite provided herein contains no greater than about 0.005% by weight of potassium. In some embodiments, the potassium content in the sodium nitrite provided herein is determined using ICP-MS. In some embodiments, the potassium content in the sodium nitrite provided herein is determined using FES.

In yet another embodiment, the sodium nitrite provided herein contains no greater than about 10 ppm, no greater than about 100 ppm, no greater than about 500 ppm, no greater than about 1000 ppm, or no greater than 5000 ppm of ethanol. In some embodiments, the content of organic volatile impurities is determined according to Method 467 in USP XXXII (2009).

In yet another embodiment, the sodium nitrite provided herein contains no greater than about 10 ppm, no greater than about 100 ppm, no greater than about 500 ppm, no greater than about 1000 ppm, or no greater than 3000 ppm of methanol. In some embodiments, the content of organic volatile impurities is determined according to Method 467 in USP XXXII (2009).

In yet another embodiment, the sodium nitrite provided herein contains total non-volatile organic carbon of no greater than about 2.5 ppm, no greater than about 6 ppm, no greater than about 8 ppm, no greater than about 10 ppm, no greater than about 20 ppm, no greater than about 25 ppm, or no greater than about 50 ppm. In some embodiments, the sodium nitrite provided herein contains total non-volatile organic carbon (NVOC) or equivalent non-purgeable organic carbon (NPOC) of no greater than about 10 ppm. In some embodiments, the sodium nitrite provided herein contains total non-volatile organic carbon of no greater than about 7.9 ppm. In some embodiments, the sodium nitrite provided herein contains total non-volatile organic carbon of no greater than about 5.6 ppm. In some embodiments, the total non-volatile organic carbon in the sodium nitrite provided herein is determined using methods described herein.

In yet another embodiment, the sodium nitrite provided herein contains no greater than about 0.05 ppm of mercury. In some embodiments, the mercury content in the sodium nitrite provided herein is determined using ICP-MS. In some embodiments, the mercury content in the sodium nitrite provided herein is determined using ICP-OES. In some embodiments, the mercury content in the sodium nitrite provided herein is determined according to Method 261 in USP XXXII (2009).

In yet another embodiment, the sodium nitrite provided herein contains no greater than about 2 ppm of aluminum. In yet another embodiment, the sodium nitrite provided herein contains no greater than about 0.2 ppm of aluminum. In some embodiments, the aluminum content in the sodium nitrite provided herein is determined using ICP-MS. In some embodiments, the aluminum content in the sodium nitrite provided herein is determined using ICP-OES. In some embodiments, the aluminum content in the sodium nitrite provided herein is determined according to Method 206 in USP XXXII (2009).

In yet another embodiment, the sodium nitrite provided herein contains no greater than about 3 ppm of arsenic. In yet another embodiment, the sodium nitrite provided herein contains no greater than about 1 ppm of arsenic. In some embodiments, the arsenic content in the sodium nitrite provided herein is determined using ICP-MS. In some embodiments, the arsenic content in the sodium nitrite provided herein is determined using ICP-OES. In some embodiments, the arsenic content in the sodium nitrite provided herein is determined according to Method 211 in USP XXXII (2009).

In yet another embodiment, the sodium nitrite provided herein contains no greater than about 10 ppm (0.001% by weight) of an anti-caking agent. In some embodiments, the anti-caking agent is sodium alkyl-naphthalene sulfonate. In some embodiments, the amount of sodium alkyl-naphthalene sulfonate in the sodium nitrite provided herein is quantitated using mass spectrometry and liquid chromatography method as described herein.

In yet another embodiment, the sodium nitrite provided herein contains no greater than about 0.003% by weight of selenium. In some embodiments, the selenium content in the sodium nitrite provided herein is determined using ICP-MS. In some embodiments, the selenium content in the sodium nitrite provided herein is determined using ICP-OES. In some embodiments, the selenium content in the sodium nitrite provided herein is determined according to Method 291 in USP XXXII (2009).

In yet another embodiment, the total aerobic count of microbial load in the sodium nitrite provided herein is no greater than about 100 CFU/g. The total aerobic count of microbial load in the sodium nitrite provided herein is quantitated according to Method 61 in USP XXXII (2009).

In yet another embodiment, the total yeast and mold count in the sodium nitrite provided herein is no greater than about 20 CFU/g. The total yeast and mold count in the sodium nitrite provided herein is quantitated according to Method 61 in USP XXXII (2009).

In yet another embodiment, the sodium nitrite provided herein contains no greater than about 0.25 EU/mg of bacterial endotoxins. The amount of bacterial endotoxins in the sodium nitrite provided herein is quantitated according to Method 85 in USP XXXII (2009).

In yet another embodiment, the sodium nitrite provided herein is characterized by one or more of the following:
containing no less than about 97% by weight and/or no greater than about 101% by weight of sodium nitrite according to USP colorimetric assay (USP XXXII (2009));
having a positive identification test for sodium;
having a positive identification test for nitrite;
having a pH between about 7 to about 9 when measured in a 10% solution at 25° C.;
having a loss on drying of no greater than about 0.25% by weight;
having water content of no greater than about 0.5% by weight;
having heavy metal content of no greater than about 10 ppm;
containing no greater than about 0.4% by weight of sodium nitrate;
containing no greater than about 0.02% by weight of sodium carbonate;
containing no greater than about 0.005% by weight of insoluble matter;
containing no greater than about 0.005% by weight of chloride;
containing no greater than about 0.01% by weight of sulfate;
containing no greater than about 0.001% by weight of iron;
containing no greater than about 0.01% by weight of calcium;
containing no greater than about 0.005% by weight of potassium;
containing no greater than about 0.1% by weight ethanol or no greater than about 10 ppm, no greater than about 100 ppm, no greater than about 500 ppm, no greater than about 1000 ppm, or no greater than 5000 ppm of ethanol;
containing no greater than about 10 ppm, no greater than about 100 ppm, no greater than about 500 ppm, no greater than about 1000 ppm, or no greater than 3000 ppm of methanol;
having total non-volatile organic carbon or equivalent of no greater than about 2.5 ppm, no greater than about 5.6 ppm, no greater than about 6 ppm, no greater than about 7.9 ppm, no greater than about 8 ppm, no greater than about 10 ppm, no greater than about 20 ppm, no greater than about 25 ppm, or no greater than about 50 ppm; and in one embodiment, no greater than about 10 ppm;
containing no greater than about 0.05 ppm of mercury;
containing no greater than about 2 ppm of aluminum;
containing no greater than about 3 ppm of arsenic;
containing no greater than about 10 ppm of an anti-caking agent;
containing no greater than about 0.003% of selenium (ICP-OES or equivalent);
having a total aerobic count of microbial load of no greater than about 100 CFU/g;
having a total yeast and mold count of no greater than about 20 CFU/g;
containing no greater than about 0.25 EU/mg of bacterial endotoxins.

In one embodiment, provided herein is sodium nitrite having one or more of the characteristics referenced herein.

Methods of Maintaining Physiological Level of Nitrite

Provided herein are methods for maintaining physiological levels of nitrite in a subject undergoing hemodialysis, comprising intradialytically contacting said subject's blood with a dialyzer membrane that is also in contact with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

Also provided herein are methods for maintaining physiological levels of nitrite in a subject undergoing hemodialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In one embodiment, the subject is a mammal. In another embodiment, the subject is a human.

In one embodiment, the physiological level of nitrite in said subject is no more than about 1 micromolar. In another embodiment, the physiological level of nitrite in said subject is between about 100 nanomolar and about 700 nanomolar. In yet another embodiment, the physiological level of nitrite in said subject is between about 200 nanomolar and about 500 nanomolar. In yet another embodiment, the physiological level of nitrite in said subject is between about 250 nanomolar and about 400 nanomolar. In yet another embodiment, the physiological level of nitrite in said subject is about 300 nanomolar.

In one embodiment, the concentration of nitrite in said nitrite-spiked dialysate is no more than about 1 micromolar. In another embodiment, the concentration of nitrite in said nitrite-spiked dialysate is between about 100 nanomolar and about 700 nanomolar. In yet another embodiment, the concentration of nitrite in said nitrite-spiked dialysate is between about 200 nanomolar and about 500 nanomolar. In yet another embodiment, the concentration of nitrite in said nitrite-spiked dialysate is between about 250 nanomolar and about 400 nanomolar. In yet another embodiment, the concentration of nitrite in said nitrite-spiked dialysate is about 300 nanomolar.

In some embodiments, the aqueous solution comprising sodium nitrite comprises no more than about 1 mg/L, about 2 mg/L, about 3 mg/L, about 4 mg/L, about 5 mg/L, about 6 mg/L, about 7 mg/L, about 8 mg/L, about 9 mg/L, or about 10 mg/L of sodium nitrite.

In some embodiments, the water comprises no more than about about 1 mg/L, about 2 mg/L, about 3 mg/L, about 4 mg/L, about 5 mg/L, about 6 mg/L, about 7 mg/L, about 8 mg/L, about 9 mg/L or about 10 mg/L of nitrite.

In one embodiment, the aqueous solution comprising sodium nitrite is added to said unspiked dialysate through a valve that is attached to dialysate tubing at a location before said tubing connects to the dialyzer. In another embodiment, said unspiked dialysate flows through said dialysis tubing at a rate between about 200 mL/min and about 1000 mL/min. In yet another embodiment, said unspiked dialysate flows through said dialysis tubing at a rate between about 300 mL/min and about 900 mL/min. In yet another embodiment, said unspiked dialysate flows through said dialysis tubing at a rate between about 400 mL/min and about 800 mL/min. In yet another embodiment, said unspiked dialysate flows through said dialysis tubing at a rate between about 500 mL/min and about 700 mL/min. In yet another embodiment, said unspiked dialysate flows through said dialysis tubing at a rate about 600 mL/min.

In one embodiment, the aqueous solution comprising sodium nitrite is added through the valve to the unspiked dialysate at a rate between about 0 mL/hr and about 750 mL/hr, at a rate between about 50 mL/hr and about 650 mL/hr, at a rate between about 100 mL/hr and about 550 mL/hr, at a rate between about 150 mL/hr and about 450 mL/hr, or at a rate between about 200 mL/hr and about 350 mL/hr. In another embodiment, the aqueous solution comprising sodium nitrite is added through the valve to the unspiked dialysate at a rate about 250 mL/hr.

In yet another embodiment, the pH of said nitrite-spiked dialysate is between about 7.0 and about 8.0. In yet another embodiment, the pH of said nitrite-spiked dialysate is between about 7.1 and about 8.0. In yet another embodiment, the pH of said nitrite-spiked dialysate is between about 7.3 and about 8.0. In yet another embodiment, the pH of said nitrite-spiked dialysate is between about 7.3 and about 7.5. In yet another embodiment, the pH of said nitrite-spiked dialysate is about 7.4.

In yet another embodiment, said subject is a human with chronic renal failure. In another embodiment, the said subject is a human with acute renal failure.

In yet another embodiment, said subject undergoes hemodialysis from one to ten times per week. In yet another embodiment, the said subject undergoes hemodialysis from three to seven times per week.

In certain embodiments, the methods provided herein return and/or maintain the subject's plasma levels of nitrite to normal physiological levels.

Methods of Prevention

1. Methods of Preventing Myocardial Infarction

In some embodiments, provided herein are methods for preventing myocardial infarction in a subject undergoing dialysis, comprising intradialytically contacting said subject's blood with a dialyzer membrane that is also in contact with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, further provided herein are methods for preventing myocardial infarction in a subject undergoing hemodialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In one embodiment, the subject is a mammal. In another embodiment, the subject is a human.

In certain embodiments, the methods provided herein return and/or maintain the subject's plasma levels of nitrite to normal physiological levels.

2. Methods of Preventing Sudden Cardiac Death

In some embodiments, provided herein are methods for preventing sudden cardiac death in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, further provided herein are methods for preventing sudden cardiac death in a subject undergoing hemodialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In one embodiment, the subject is a mammal. In another embodiment, the subject is a human.

In certain embodiments, the methods provided herein return and/or maintain the subject's plasma levels of nitrite to normal physiological levels.

3. Methods of Preventing Stroke

In some embodiments, provided herein are methods for preventing stroke in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, further provided herein are methods for preventing stroke in a subject undergoing hemodialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In one embodiment, the subject is a mammal. In another embodiment, the subject is a human.

In certain embodiments, the methods provided herein return and/or maintain the subject's plasma levels of nitrite to normal physiological levels.

4. Methods of Preventing Cardiovascular Disease

In some embodiments, provided herein are methods for preventing cardiovascular disease that is characterized by tissue ischemia including angina, cerebral vasospasm, claudication, critical limb ischemia, peripheral vascular disease, and sickle cell crisis in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, further provided herein are methods for preventing cardiovascular disease that is characterized by tissue ischemia including angina, cerebral vasospasm, claudication, critical limb ischemia, peripheral vascular disease, and sickle cell crisis in a subject undergoing dialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In one embodiment, the subject is a mammal. In another embodiment, the subject is a human.

In certain embodiments, the methods provided herein return and/or maintain the subject's plasma levels of nitrite to normal physiological levels.

5. Methods of Preventing High Blood Pressure, Pulmonary Hypertension, and Renal Hypertension In some embodiments, provided herein are methods for preventing high blood pressure, pulmonary hypertension, and renal hypertension in a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, further provided herein are methods for preventing high blood pressure, pulmonary hypertension, and renal hypertension in a subject undergoing dialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In some embodiments, the pulmonary hypertension is neonatal pulmonary hypertension, primary pulmonary hypertension, or secondary pulmonary hypertension.

In one embodiment, the subject is a mammal. In another embodiment, the subject is a human.

In certain embodiments, the methods provided herein return and/or maintain the subject's plasma levels of nitrite to normal physiological levels.

In certain embodiments, the embodiments in the remaining paragraphs of this section apply to all methods provided herein.

In one embodiment, the physiological level of nitrite in said subject is no more than about 1 micromolar. In another embodiment, the physiological level of nitrite in said subject is between about 100 nanomolar and about 700 nanomolar. In yet another embodiment, the physiological level of nitrite in said subject is between about 200 nanomolar and about 500 nanomolar. In yet another embodiment, the physiological level of nitrite in said subject is between about 250 nanomolar and about 400 nanomolar. In yet another embodiment, the physiological level of nitrite in said subject is about 300 nanomolar.

In one embodiment, the concentration of nitrite in said nitrite-spiked dialysate is no more than about 1 micromolar. In another embodiment, the concentration of nitrite in said nitrite-spiked dialysate is between about 100 nanomolar and about 700 nanomolar. In yet another embodiment, the concentration of nitrite in said nitrite-spiked dialysate is between about 200 nanomolar and about 500 nanomolar. In yet another embodiment, the concentration of nitrite in said nitrite-spiked dialysate is between about 250 nanomolar and about 400 nanomolar. In yet another embodiment, the concentration of nitrite in said nitrite-spiked dialysate is about 300 nanomolar.

In some embodiments, the aqueous solution comprising sodium nitrite comprises no more than about 1 mg/L, about 2 mg/L, about 3 mg/L, about 4 mg/L, about 5 mg/L, about 6 mg/L, about 7 mg/L, about 8 mg/L, about 9 mg/L, or about 10 mg/L of nitrite.

In some embodiments, the water comprises no more than about 1 mg/L, about 2 mg/L, about 3 mg/L, about 4 mg/L, about 5 mg/L, about 6 mg/L, about 7 mg/L, about 8 mg/L, about 9 mg/L or about 10 mg/L of nitrite.

In one embodiment, the aqueous solution comprising sodium nitrite is added to said unspiked dialysate through a valve that is attached to dialysate tubing at a location before said tubing connects to the dialyzer. In another embodiment, said unspiked dialysate flows through said dialysis tubing at a rate between about 200 mL/min and about 1000 mL/min. In yet another embodiment, said unspiked dialysate flows through said dialysis tubing at a rate between about 300 mL/min and about 900 mL/min. In yet another embodiment, said unspiked dialysate flows through said dialysis tubing at a rate between about 400 mL/min and about 800 mL/min. In yet another embodiment, said unspiked dialysate flows through said dialysis tubing at a rate between about 500 mL/min and about 700 mL/min. In yet another embodiment, said unspiked dialysate flows through said dialysis tubing at a rate about 600 mL/min.

In one embodiment, the aqueous solution comprising sodium nitrite is added through the valve to the unspiked dialysate at a rate between about 0 mL/hr and about 750 mL/hr, at a rate between about 50 mL/hr and about 650 mL/hr, at a rate between about 100 mL/hr and about 550 mL/hr, at a rate between about 150 mL/hr and about 450 mL/hr, or at a rate between about 200 mL/hr and about 350 mL/hr. In another embodiment, the aqueous solution comprising sodium nitrite is added through the valve to the unspiked dialysate at a rate about 250 mL/hr.

In yet another embodiment, the pH of said nitrite-spiked dialysate is between about 7.0 and about 8.0. In yet another embodiment, the pH of said nitrite-spiked dialysate is between about 7.1 and about 8.0. In yet another embodiment, the pH of said nitrite-spiked dialysate is between about 7.3 and about 8.0. In yet another embodiment, the pH of said nitrite-spiked dialysate is between about 7.3 and about 7.5. In yet another embodiment, the pH of said nitrite-spiked dialysate is about 7.4.

In yet another embodiment, the said subject is a human with chronic renal failure. In another embodiment, the said subject is a human with acute renal failure.

In yet another embodiment, the said subject undergoes hemodialysis from one to ten times per week. In yet another embodiment, the said subject undergoes hemodialysis from three to seven times per week.

In one embodiment, the nitrite-spiked dialysate has less than about 10%, about 9%, about 8%, about 7%, about 6%, about 5%, about 4%, about 3%, about 2%, about 1%, about 0.4%, or about 0.1% decomposition of nitrite as reflected by the nitrate content measured in a sample taken from Detection Point "pre" (100) or Detection point "post" (110).

Methods of Administration

In some embodiments, provided herein are methods for administering sodium nitrite to a subject undergoing dialysis, comprising intradialytically contacting said subject's blood with a dialyzer membrane that is also in contact with a nitrite-spiked dialysate, wherein an aqueous solution comprising sodium nitrite is added to said unspiked dialysate as the unspiked dialysate flows from a dialysis machine to a dialyzer membrane, wherein said unspiked dialysate comprise a mixture of water, an acid concentrate solution, and a bicarbonate concentrate solution, and wherein said nitrite-spiked dialysate has a pH greater than about 7.0.

In some embodiments, further provided herein are methods for administering sodium nitrite to a subject undergoing hemodialysis, comprising intradialytically contacting said subject's blood with a nitrite-spiked dialysate, wherein an aqueous solution comprising sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

In one embodiment, the nitrite-spiked dialysate has less than about 10%, about 9%, about 8%, about 7%, about 6%, about 5%, about 4%, about 3%, about 2%, about 1%, about 0.4%, or about 0.1% decomposition of nitrite as reflected by the nitrate content measured in a sample taken from Detection Point "pre" (100) or Detection point "post" (110).

Combination Therapy

In some embodiments, the sodium nitrite provided herein may also be combined or used in combination with other therapeutic agents useful in the treatment and/or prevention of the diseases and conditions provided herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks before), concomitantly with, or subsequent to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks after) the administration of a second therapy (e.g., a prophylactic or therapeutic agent) to the subject. Triple therapy is also contemplated herein.

As used herein, the term "synergistic" includes a combination of the sodium nitrite provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The sodium nitrite provided herein can be administered in combination or alternation with another therapeutic agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The sodium nitrite provided herein can be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; cyclooxygenase-2 (COX-2) inhibitors, such as celecoxib and rofecoxib; and miscellaneous agents such as, sodium thiosulfate, hydroxyurea, procarbazine, mitotane, hexamethylmelamine, gold compounds, low-molecular weight medications, low-molecular weight vitamins, and platinum coordination complexes, such as cisplatin, satraplatin, and carboplatin.

The sodium nitrite provided herein can be administered in combination with other solutes that are naturally present in human blood including copper, fluoride, iodine, iron, manganese, magnesium, phosphorus, selenium, thiosulfate, and zinc.

The disclosure will be further understood by the following non-limiting examples.

EXAMPLES

As used herein, the symbols and conventions used in these experiments, processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); nM (nanomolar); mmol (millimoles); eq. (equivalent); hr or hrs (hours); min (minutes).

For all of the following experiments and the following example, standard work-up and purification methods known to those skilled in the art can be utilized. Unless otherwise indicated, all temperatures are expressed in ° C. (degrees Centigrade). All reactions conducted at room temperature unless otherwise noted. Methodologies illustrated in the following examples are intended to exemplify the applicable chemistry through the use of specific examples and are not indicative of the scope of the invention.

Stability Experiments

Results of the following stability experiments (Example 1 to 4) exemplify the instability of nitrite in aqueous solution when acid is added and also the instability of nitrite when mixed with a solution comprising an acid concentrate solution and a bicarbonate concentrate solution in the preparation of a dialysate for dialysis.

Concentration of nitrite in samples was assayed by ion chromatography. The ion chromatograph was equipped with a conductivity detector, self-regenerating suppression system, eluent generator, and a Dionex IonPacAS19 analytical column. The nitrite concentration in the samples was measured and calculated against an external sodium nitrite standard. USP Sodium Nitrite Reference Standard (Item Number 1614454) was the testing standard (United States Pharmacopeia. Rockville, Md.).

Example 1

The International Chemical Safety Card for sodium nitrite indicates that the chemical decomposes on contact with acid to produce toxic fumes of nitrogen oxides (International Programme on Chemical Safety accessed online at www.ilo.org/dyn/icsc/showcard.displav?p_card_id-1120).

Example 1 was performed to determine the stability of sodium nitrite in aqueous solution when acid is added. A 100 mL sample of sodium nitrite solution with a concentration of 30 mg/mL was tested for the presence of nitrogen oxide gases ($NO$, $NO_2$, $N_2O_3$, and $N_2O_4$) using an Orion Model 95-46 Nitrogen Oxide (NOx) electrode and a pH meter. With constant stirring, the mV reading with the NOx electrode and pH reading with the pH electrode were recorded after successive additions of 100 μL of either 0.02 N or 1 N hydrochloric acid. The initial pH of the sodium nitrite solution was 8.73. When the pH of the sodium nitrite solution decreased to 6.7 along with successive addition of hydrochloric acid, nitrogen oxides was detected (detection limit of 1 ppm NOx). The response of the Nitrogen Oxide electrode increased from 8.0 mV to 99.5 mV when the pH of the sodium nitrite solution declined from 6.7 to 4.9. These results confirm that sodium nitrite decomposes when exposed to acid and that the extent of decomposition is generally inversely proportional to the pH.

Example 2

Example 2 was performed to determine the stability of sodium nitrite in dialysate bicarbonate concentrate solution. At room temperature, 300 mg sodium nitrite was added to 7,700 mL of dialysate bicarbonate concentrate solution. The nitrite concentration of the dialysate bicarbonate concentrate solution was analyzed by ion chromatography 1) before addition of sodium nitrite; 2) 5 minutes after the addition of sodium nitrite; and 3) 2 hours after the addition of sodium nitrite. The results presented in Table 1 show that nitrite is stable and does not degrade to form nitrate when added to dialysate bicarbonate concentrate solution.

Example 3

Example 3 was performed to further determine the stability of nitrite in the mixture of sodium nitrite and dialysate bicarbonate concentrate solution from Example 2 when mixed with an acid concentrate solution within a dialysis machine.

A dialysis machine mixed the dialysate bicarbonate concentrate solution (with sodium nitrite added from Example 2), an acid concentrate solution and purified water as the dialysis machined mixes dialysate in clinical practice, with the dilution ratio of 1 part of the acid concentrate solution, 1.72 parts of the bicarbonate concentrate solution, and 42.38 parts of purified water. The dialysis machine used for this experiment was a Fresenius 2008K hemodialysis machine (Fresenius Medical Care, Waltham, Mass.). The machine was primed in bypass mode (dialysate and ultrafiltration rates set at zero) using normal saline. After priming, the hemodialysis machine was run in "Therapy Mode" with the following settings: blood flow rate 300 mL/minute, dialysate flow rate 600 mL/minute, ultrafiltration rate 0 mL/minute, and ultrafiltration time 25 minutes. A sample of the mixed dialysate was collected as it exited the dialysis machine and analyzed by ion chromatography.

The results presented in Table 2 show that nitrite in the dialysate bicarbonate concentrate solution completely decomposed in the process of mixing with an acid concentrate solution within the dialysis machine.

TABLE 2

Nitrite Concentration in Dialysate after Mixing within Hemodialysis Machine

| Sample | Expected Nitrite Concentration | Nitrite Concentration by Assay | % Recovery |
|---|---|---|---|
| Mixed Dialysate + Sodium Nitrite | 1.46 mg/L | None Detected | 0% |

Example 4

Example 4 was performed to determine the stability of nitrite when sodium nitrite is added to the dialysate after the dialysate has been prepared in a laboratory. Using the dilution ratio of 1 part of the acid concentrate solution, 1.72 parts of the bicarbonate concentrate solution, and 42.38 parts of purified water, one liter of dialysate was prepared in a laboratory by adding 38.22 mL of bicarbonate concentrate solution and 22.22 mL of acid concentrate solution to 938.56 mL of purified water. The pH of the dialysate solution was

TABLE 1

Nitrite Concentration in Dialysate Bicarbonate Concentrate

| Sample | Expected Nitrite Concentration | Nitrite Concentration by Assay | % Recovery | Nitrate Concentration |
|---|---|---|---|---|
| Dialysate Bicarbonate Concentrate Solution | 0 | None Detected | NA | None Detected |
| Dialysate Bicarbonate Concentrate + Sodium Nitrite after 5 Minutes | 38.1 mg/L | 38.0 mg/L | 100% | None Detected |
| Dialysate Bicarbonate Concentrate + Sodium Nitrite Solution after 2 Hours | 38.1 mg/L | 38.5 mg/L | 101% | None Detected |

7.34 at 24.9° C. One mL of 3 mg/mL sodium nitrite solution was added to the premixed 1 L dialysate solution. After the addition of sodium nitrite solution, the pH of the dialysate solution was 7.32 at 24.4° C. A sample of the dialysate solution with added sodium nitrite was analyzed for nitrite concentration. The results presented in Table 3 show that nitrite partially decomposed after addition to a premixed dialysate solution.

TABLE 3

Nitrite Concentration in Pre-Mixed Dialysate in a Laboratory

| Sample | Expected Nitrite Concentration | Nitrite Concentration by Assay | % Recovery |
|---|---|---|---|
| Mixed Dialysate + Sodium Nitrite | 2.997 mg/L | 1.149 mg/L | 38% |

Example 5

Example 5 was performed to determine the stability of nitrite when sodium nitrite is added to the dialysate after the dialysate has been prepared within a Fresenius 2008K hemodialysis machine (Fresenius Medical Care, Waltham, Mass.). Dialysate bicarbonate concentrate solution was prepared by adding 1 package of Centrisol® MB-330 Series Sodium Bicarbonate Concentrate powder (650 g) to 7.7 liters of purified water.

The hemodialysis machine mixed the bicarbonate concentrate solution and acid concentrate solution with the dilution ratio of 1 part of an acid concentrate solution, 1.72 parts of a bicarbonate concentrate solution, and 42.38 parts of purified water. The machine was primed in bypass mode (dialysate and ultrafiltration rates set at zero) using normal saline. After priming, the hemodialysis machine was run in "Therapy Mode" with the following settings: blood flow rate 300 mL/minute, dialysate flow rate 600 mL/minute, ultrafiltration rate 0 mL/minute.

An aqueous solution of sodium nitrite was prepared by dissolving 3 mg of sodium nitrite in 1 liter of purified water. This sodium nitrite solution complied with the AAMI quality specification for nitrate (and nitrite) since the resulting sodium nitrite solution had a nitrite anion concentration of approximately 2 mg/L. The sodium nitrite solution was infused directly into dialysate tubing between the hemodialysis machine and the dialyzer via a valve (Fresensius Dialysate Sample Valve: part #650993) using an Alaris® IV Infusion Pump (Model 8100, CareFusion, San Diego, Calif.). This valve was placed in the dialysate tubing approximately eight inches upstream of the dialyzer (prefilter). Two sampling ports were placed four inches upstream (pre-dialyzer sampling port) and ten inches downstream (post-dialyzer sampling port) from the dialyzer to collect samples of dialysate for nitrate assay by ion chromatography.

The infusion pump infused the sodium nitrite solution into the tubing through the valve at a rate of 250 mL/hour (4.16 mL/minute).

Normal saline flowed into the dialyzer at a rate of 300 mL/minute from the Arterial line and exited the dialyzer through the Venous line. Samples of saline were collected from the venous side of the dialyzer.

The results presented in Table 4 show that nitrite is stable when a sodium nitrite solution mixed with dialysate within dialysate tubing when infused into the tubing at a location that is between the hemodialysis machine and the dialyzer membrane.

TABLE 4

Nitrite Concentration in Dialysate Before and After Sodium Nitrite Solution is Added to Dialysate within Dialysate Tubing Before Dialysate Contacting the Dialyzer Membrane

| Sample | Nitrite Concentration* Before Addition of Sodium Nitrite (Time = 0 Min) | Nitrite Concentration* After Addition of Sodium Nitrite (Time = 60 Min) |
|---|---|---|
| Dialysate + Sodium Nitrite Solution (Before Dialyzer) | 0 | 451 nM |
| Dialysate + Sodium Nitrite Solution (After Dialyzer) | 0 | 235 nM |
| Saline Solution (After Dialyzer) | 0 | 183 nM |

*Average results from two samples

The results presented in Table 4 show that nitrite can either pass along or pass through a dialyzer if the nitrite is added to the unspiked dialysate from the hemodialysis machine at a location between the hemodialysis machine and the dialyzer membrane.

The example set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for reducing the risk of cardiovascular disease that is characterized by tissue ischemia selected from the group consisting of angina, cerebral vasospasm, claudication, critical limb ischemia, peripheral vascular disease, and sickle cell crisis in a subject undergoing dialysis, comprising intradialytically contacting said subject's blood with a dialyzer membrane that is also in contact with a nitrite-spiked dialysate, wherein an aqueous solution comprising a therapeutically effective amount of sodium nitrite is added to an unspiked dialysate as the unspiked dialysate flows from a dialysis machine to a dialyzer membrane, wherein said unspiked dialysate comprises a mixture of water, an acid concentrate solution, and a bicarbonate concentrate solution, and wherein said nitrite-spiked dialysate has a pH greater than about 7.0.

2. The method of claim 1, wherein the physiological level of nitrite in said subject is no more than about 1 micromolar.

3. The method of claim 1, wherein the physiological level of nitrite in said subject is between about 200 nanomolar and about 500 nanomolar.

4. The method of claim 1, wherein the physiological level of nitrite in said subject is about 300 nanomolar.

5. The method of claim 1, wherein the concentration of nitrite in said nitrite-spiked dialysate is no more than about 1 micromolar.

6. The method of claim 1, wherein the concentration of nitrite in said nitrite-spiked dialysate is between about 200 nanomolar and about 500 nanomolar.

7. The method of claim 1, wherein the concentration of nitrite in said nitrite-spiked dialysate is about 300 nanomolar.

8. The method of claim 1, wherein said aqueous solution comprising sodium nitrite comprises no more than about 3 mg/L of sodium nitrite.

9. The method of claim 1, wherein said water comprises no more than about 2 mg/L of nitrite.

10. The method of claim 1, wherein said aqueous solution comprising sodium nitrite is added to said unspiked dialysate through a valve that is attached to dialysate tubing at a location before said tubing connects to the dialyzer.

11. The method of claim 10, wherein said unspiked dialysate flows through said dialysis tubing at a rate between about 500 mL/min and about 700 mL/min.

12. The method of claim 10, wherein said unspiked dialysate flows through said dialysis tubing at a rate of about 600 mL/min.

13. The method of claim 10, wherein said aqueous solution comprising sodium nitrite is added through said valve to said unspiked dialysate at a rate between about 100 mL/hr and about 550 mL/hr.

14. The method of claim 10, wherein said aqueous solution comprising sodium nitrite is added through said valve to said unspiked dialysate at a rate of about 250 mL per hour.

15. The method of claim 1, wherein the pH of said nitrite-spiked dialysate is between about 7.3 and about 7.5.

16. The method of claim 1, wherein the pH of said nitrite-spiked dialysate is about 7.4.

17. The method of claim 1, wherein said subject is a human with chronic renal failure.

18. The method of claim 1, wherein said subject is a human with acute renal failure.

19. The method of claim 1, wherein said subject undergoes dialysis from three to seven times per week.

* * * * *